United States Patent
Blythe et al.

(10) Patent No.: US 6,705,316 B2
(45) Date of Patent: Mar. 16, 2004

(54) PULMONARY DOSING SYSTEM AND METHOD

(75) Inventors: Kevin Sanford Blythe, Lancaster, OH (US); Anthony Rocco Imondi, Westerville, OH (US); Daniel Duane Meek, Canal Winchester, OH (US); Andrew O. Ross, Worthington, OH (US)

(73) Assignee: Battelle Pulmonary Therapeutics, Inc., Columbus, OH (US)

( * ) Notice: Subject to any disclaimer, the term of this patent is extended or adjusted under 35 U.S.C. 154(b) by 3 days.

(21) Appl. No.: 10/095,250

(22) Filed: Mar. 11, 2002

(65) Prior Publication Data

US 2003/0168062 A1 Sep. 11, 2003

(51) Int. Cl.[7] .................................................. A62B 7/00
(52) U.S. Cl. ........................... 128/204.18; 128/200.18; 128/203.12
(58) Field of Search ................ 128/200.18, 203.12, 128/203.14, 204.23; 239/504, 590, 590.5

(56) References Cited

U.S. PATENT DOCUMENTS

| | | | | |
|---|---|---|---|---|
| 1,150,238 A | * | 8/1915 | Bray | 239/338 |
| 1,263,079 A | * | 4/1918 | Leon | 239/338 |
| 1,836,505 A | * | 12/1931 | Pritchard | 239/500 |
| 2,562,930 A | * | 8/1951 | Mapes | 169/75 |
| 2,625,156 A | * | 1/1953 | Gauchard | 128/200.18 |
| 2,678,044 A | * | 5/1954 | Szekely et al. | 128/200.18 |
| 2,785,679 A | * | 3/1957 | Wullschleger | 128/200.18 |
| 2,826,454 A | * | 3/1958 | Counda | 239/338 |
| 3,051,397 A | * | 8/1962 | Hanson | 239/432 |
| 3,062,456 A | * | 11/1962 | Thompson et al. | 239/590.5 |
| 3,236,458 A | * | 2/1966 | Ramis | 239/338 |
| 3,301,255 A | * | 1/1967 | Thompson | 128/200.18 |
| 3,302,374 A | * | 2/1967 | Szckely | 96/260 |
| 3,522,806 A | * | 8/1970 | Szekely | 128/200.18 |
| 3,529,941 A | * | 9/1970 | Tobiassen et al. | 422/138 |
| 3,838,686 A | * | 10/1974 | Szekely | 128/200.18 |
| 3,945,378 A | * | 3/1976 | Paluch | 128/201.13 |
| 4,026,285 A | * | 5/1977 | Jackson | 128/200.17 |
| 4,106,503 A | * | 8/1978 | Rosenthal et al. | 128/200.18 |
| 4,344,574 A | * | 8/1982 | Meddings et al. | 239/338 |
| 4,402,315 A | * | 9/1983 | Tsuda et al. | 128/200.18 |
| 4,429,835 A | * | 2/1984 | Brugger et al. | 239/338 |
| 4,534,343 A | | 8/1985 | Nowacki et al. | |
| 4,566,452 A | | 1/1986 | Farr | |
| 4,660,547 A | * | 4/1987 | Kremer, Jr. | 600/3 |
| 4,677,975 A | * | 7/1987 | Edgar et al. | 128/200.14 |
| 4,690,332 A | * | 9/1987 | Hughes | 239/338 |
| 4,790,305 A | | 12/1988 | Zoltan et al. | |
| 4,805,609 A | | 2/1989 | Roberts et al. | |
| 4,819,629 A | * | 4/1989 | Jonson | 128/203.22 |
| 4,823,784 A | | 4/1989 | Bordoni et al. | |
| 4,869,103 A | * | 9/1989 | Jerman | 73/198 |
| 4,911,157 A | | 3/1990 | Miller | |

(List continued on next page.)

OTHER PUBLICATIONS

Feddah, M.R. et al., *In–Virtro Characterisation of Metered Dose Inhaler Versus Dry Powder Inhaler Glucocorticoid Products: Influenced of Inspiratory Flow Rates*, J. Pharm. Pharmaceut. Sci. 3(3):317–324 (Oct. 2000).

Elliott, R., *Parenteral absorption of Insulin from the lug in diabetic children*, Aust. Pediatr. J. 23, 293–297 (1997).

Primary Examiner—Aaron J. Lewis
(74) Attorney, Agent, or Firm—Thompson Hine LLP

(57) ABSTRACT

A pulmonary dosing system and method for supplying to a patient a predetermined amount of respirable therapeutically active material is disclosed. The system comprises a patient interface to introduce the material into the patient's lungs and an apparatus for providing pulsed amounts of the material to a plenum chamber. The plenum chamber has a diffuser baffle which increases the efficiency of the dosing system by preventing axial flow of the active material thereby utilizing the available volume of the chamber for holding the aerosolized drug prior to inhalation.

35 Claims, 9 Drawing Sheets

U.S. PATENT DOCUMENTS

| | | |
|---|---|---|
| 4,926,852 A | 5/1990 | Zoltan et al. |
| 4,940,051 A | 7/1990 | Lankinen |
| 4,953,545 A | 9/1990 | McCarty |
| 4,972,830 A | 11/1990 | Wong et al. |
| 5,012,803 A | 5/1991 | Foley et al. |
| 5,036,840 A | 8/1991 | Wallace |
| 5,040,527 A | 8/1991 | Larson et al. |
| 5,042,467 A | 8/1991 | Foley |
| 5,054,478 A | 10/1991 | Grychowski et al. |
| 5,062,419 A | 11/1991 | Rider |
| 5,063,922 A * | 11/1991 | Hakkinen ............... 128/200.16 |
| 5,080,093 A * | 1/1992 | Raabe et al. ........... 128/203.12 |
| 5,113,855 A | 5/1992 | Newhouse |
| 5,165,391 A | 11/1992 | Chiesi et al. |
| 5,178,138 A | 1/1993 | Walstrom et al. |
| 5,186,166 A | 2/1993 | Riggs et al. |
| 5,241,954 A * | 9/1993 | Glenn ................... 128/200.18 |
| 5,297,543 A | 3/1994 | Larson et al. |
| 5,309,900 A * | 5/1994 | Knoch et al. .......... 128/200.14 |
| 5,312,331 A * | 5/1994 | Knoepfler ................... 604/500 |
| 5,322,057 A * | 6/1994 | Raabe et al. ........... 128/203.12 |
| 5,458,135 A * | 10/1995 | Patton et al. .......... 128/200.14 |
| 5,458,136 A | 10/1995 | Jaser et al. |
| 5,476,093 A | 12/1995 | Lankinen |
| 5,503,139 A | 4/1996 | McMahon et al. |
| 5,617,844 A * | 4/1997 | King ..................... 128/200.18 |
| 5,630,409 A | 5/1997 | Bono et al. |
| 5,645,049 A | 7/1997 | Foley et al. |
| 5,676,130 A | 10/1997 | Gupte et al. |
| 5,711,292 A | 1/1998 | Hammarlund |
| 5,724,959 A | 3/1998 | McAughey et al. |
| 5,727,542 A | 3/1998 | King |
| 5,738,087 A | 4/1998 | King |
| 5,752,502 A | 5/1998 | King |
| 5,775,320 A * | 7/1998 | Patton et al. .......... 128/200.14 |
| 5,813,397 A | 9/1998 | Goodman et al. |
| 5,816,240 A | 10/1998 | Komesaroff |
| 5,826,570 A | 10/1998 | Goodman et al. |
| 5,848,588 A | 12/1998 | Foley et al. |
| 5,875,774 A | 3/1999 | Clementi et al. |
| 5,884,620 A | 3/1999 | Gonda et al. |
| 5,934,272 A | 8/1999 | Lloyd et al. |
| 5,934,273 A | 8/1999 | Andersson et al. |
| 5,941,240 A | 8/1999 | Gonda et al. |
| 5,957,124 A | 9/1999 | Lloyd et al. |
| 6,012,450 A | 1/2000 | Rubsamen |
| 6,039,042 A | 3/2000 | Sladek |
| 6,041,777 A | 3/2000 | Faithfull et al. |
| 6,070,573 A | 6/2000 | Howe et al. |
| 6,076,519 A | 6/2000 | Johnson |
| 6,085,742 A | 7/2000 | Wachter et al. |
| 6,098,620 A | 8/2000 | Lloyd et al. |
| 6,103,270 A | 8/2000 | Johnson et al. |
| 6,109,261 A | 8/2000 | Clarke et al. |
| 6,116,237 A | 9/2000 | Schultz et al. |
| 6,131,567 A | 10/2000 | Gonda et al. |
| 6,138,668 A | 10/2000 | Patton et al. |
| 6,167,880 B1 | 1/2001 | Gonda et al. |
| 6,250,298 B1 | 6/2001 | Gonda et al. |
| 6,250,300 B1 | 6/2001 | Andersson et al. |
| 6,257,233 B1 | 7/2001 | Burr et al. |
| 6,260,549 B1 | 7/2001 | Sosiak |
| 6,263,872 B1 | 7/2001 | Schuster et al. |
| 6,269,810 B1 | 8/2001 | Brooker et al. |
| 6,273,088 B1 | 8/2001 | Hillsman |
| 6,286,506 B1 | 9/2001 | MacAndrew et al. |
| 6,289,892 B1 | 9/2001 | Faithfull et al. |
| 6,293,279 B1 | 9/2001 | Schmidt et al. |
| 6,308,703 B1 | 10/2001 | Alving et al. |
| 6,308,705 B1 | 10/2001 | Rupprecht et al. |
| 6,314,956 B1 | 11/2001 | Stamler et al. |

* cited by examiner

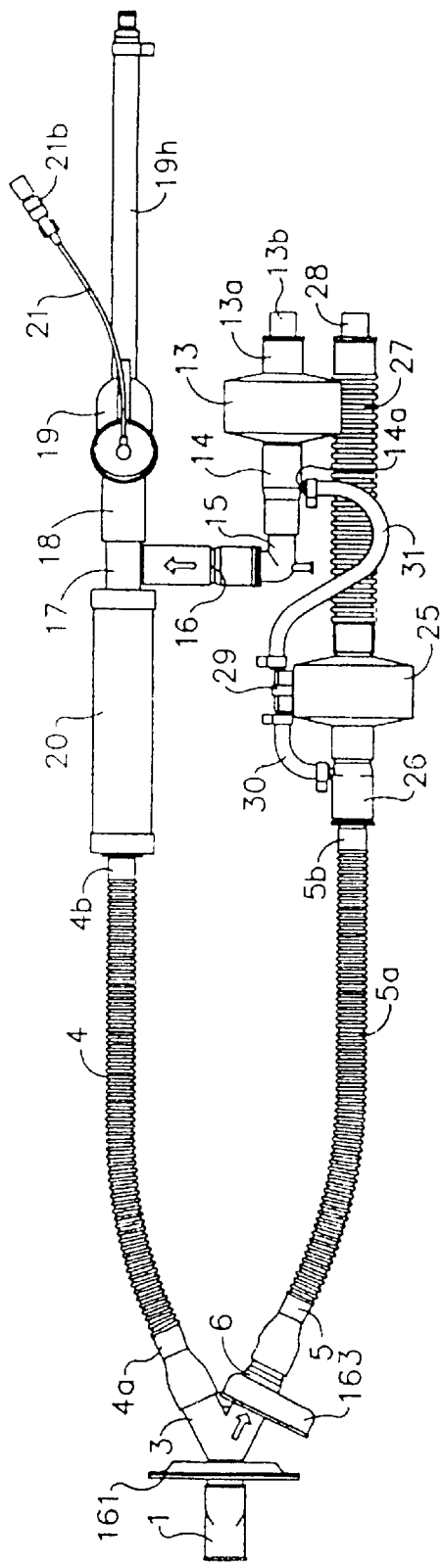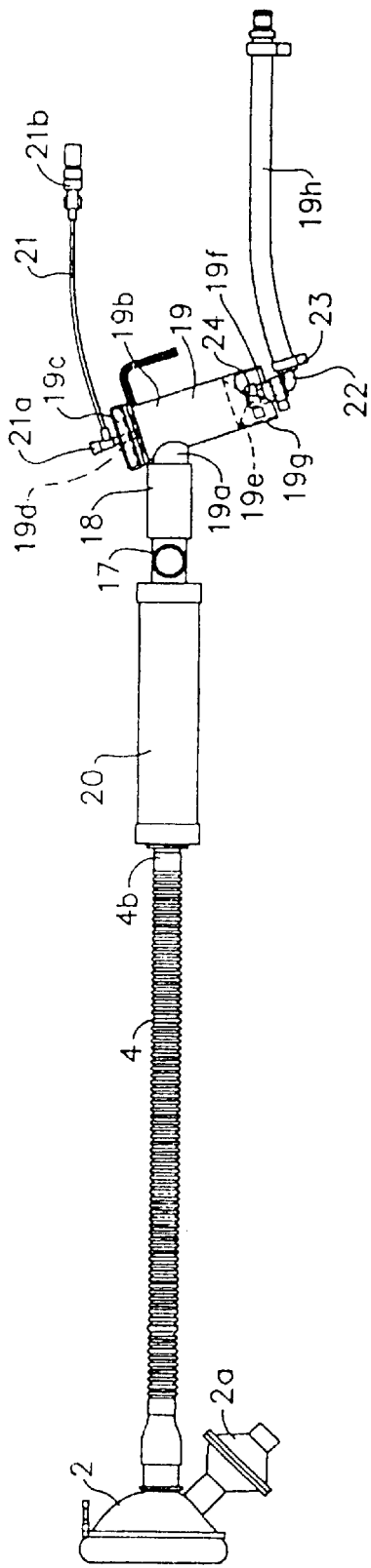
FIG. 2
FIG. 3

PULMONARY DOSING SYSTEM AND METHOD

TECHNICAL FIELD

The present invention relates to an improvement in pulmonary dosing systems of the type taught in U.S. Pat. No. 6,269,810, wherein a diffuser baffle is provided in the plenum of the pulmonary dosing system to improve dosing efficiency.

The invention relates to a pulmonary dosing system and method for supplying to a patient a predetermined amount of respirable therapeutically active material in an aerosolized form, and more particularly to such a system and method which is compact, self-contained, and capable of supplying any respirable therapeutically active material, including toxic drugs such as chemotherapy drugs, wherein a diffuser baffle is utilized in the plenum of the system to improve dosing efficiency.

BACKGROUND ART

The pulmonary dosing system described in commonly assigned U.S. Pat. No. 6,269,810 to Brooker et al. is able to contain the therapeutically active material or drug to the extent that it can safely administer toxic drugs such as chemotherapy drugs. The respirable therapeutically active material is aerosolized, typically by being entrained in pulses of air synchronized with the patient's exhalations. Except for the inhalation tube, the exhalation tube and the patient interface connected thereto, the remainder of the inhalation and exhalation portions of the system including the delivery apparatus for the therapeutically active material may be located in a sealed containment case. The containment case may be subjected to a mild vacuum from a vacuum source including a filter to further assure containment of the therapeutically active material, if necessary. Alternatively, the system may be provided with an active flow system for ensuring flow through the system. The system may be provided with a control unit containing a compressor and valve to provide pulsed air, a vacuum pump to provide the mild vacuum within the containment case, and a computer with inputs from various sensor devices together with a number of interfaces with the operator and with the patient.

One of the more advantageous features of the Brooker et al. drug delivery or pulmonary dosing system is its efficiency in delivering drugs. This may be particularly important with respect to the time spent by the patient and the support staff for each treatment and also with respect to reducing the expense of extremely costly drugs. The efficiency refers not only to the efficiency of delivering drug to the patient (not lost in the delivery system), but also to the efficiency of getting the delivered drug to penetrate deep into the lung of the patient to provide the needed therapy. The present invention may reduce the amount of aerosolized drug that may be deposited in the mouth, the upper airway, or the nasal cavity.

One of the novel features which adds to this efficiency is the combination of the nebulizer (or other aerosol-producing device), the plenum with a diffuser baffle, an air supply and the control system, which are combined to provide a metered dose of drug and air to the patient at the designated time for inhalation. In one efficient operation, the aerosol-producing device is controlled to deliver a selected volume of drug aerosol to the plenum prior to the inhalation phase of the patient. As described herein, this can be performed by sensing the exhalation phase of the patient and then providing a pulse of air to the nebulizer which results in a metered volume of aerosolized drug in the plenum. Sensing the exhalation phase of the patient may include automatic sensing or manual sensing, as by the patient or operator.

The diffuser baffle prevents axial flow of the aerosolized dose from the inlet to the outlet of the plenum, thereby more efficiently utilizing the available volume in the plenum such that the aerosolized dose is retained in the plenum and the inhalation tube until the inhalation phase is initiated. The disruption of axial flow of the aerosolized dose provided by the diffuser baffle reduces or eliminates the loss of drug into the exhale tube. The loss of drug associated with the flow of the aerosolized dose into the exhale tube prior to the start of the inhalation phase is referred to as "blow-by." This phenomenon causes inefficient operation of the pulmonary dosing system as well as loss of expensive drug. The inability to control "blow-by" interferes with the delivery of an accurate and predictable delivered dose. The diffuser baffle in the plenum improves the reproducibility with which an accurate dose can be delivered by increasing the retention of the aerosolized dose in the chamber and minimizing or eliminating "blow-by" of the drug.

DISCLOSURE OF THE INVENTION

The present invention is directed to an improved system for pulmonary dosing and, in particular, to an improved plenum useful in a pulmonary dosing system similar to that disclosed in U.S. Pat. No. 6,269,810 to Brooker et al., the contents of which are incorporated herein by reference. The plenum chamber of the present invention comprises an inlet for receiving aerosolized doses from an aerosolizer source and an outlet for connection to a patient interface, wherein the inlet and outlet are oriented along a common axis in the plenum chamber, and a diffuser baffle is positioned on that axis and interposed between the inlet and outlet. The diffuser baffle interrupts the direct flow of the aerosolized dose along the axial path between the plenum chamber inlet and outlet thereby preventing direct flow of the aerosolized dose through the chamber and possible loss of drug into the exhale tube. The aerosolized dose is diverted by the diffuser baffle thereby efficiently utilizing the available volume of the plenum chamber. The dose is held in the chamber and the inhale tube until the patient inhales.

Many pharmaceutical agents such as chemotherapy drugs are both toxic and expensive. This means that it is very important to use these drugs efficiently and safely. It has been found that the plenum shown in the Brooker patent produces an axialized flow of the medicament. The annular volumes within the chamber tend to be somewhat stagnant and aerosolized pulses can move directly through the chamber. When this occurs the dose is not used efficiently. It has been found advantageous to disrupt this flow, however, it has also been found that vortical flow that maximizes exposure of the medicament to the surface of the plenum is not desirable as the medicament may adhere to the surface of the plenum and not be inhaled by the patient.

In accordance with certain embodiments of the invention, there is provided a pulmonary dosing system and method for supplying to a patient a predetermined amount of respirable therapeutically active material. The system may comprise a patient interface to introduce the material into the patient's lungs. This interface may constitute a mouth piece, a mask and mouth tube combination, an endotracheal tube, a nasal tube, or the like. The patient interface is connected to a flexible inhalation tube and a flexible exhalation tube. The exhalation tube is connected to a filter, the outlet of which is connected to atmosphere. The inhalation tube is connected to an apparatus for providing pulsed amounts of the material entrained in filtered atmospheric air. The apparatus may comprise a nebulizer having an inlet for pulsed air, a plenum chamber with a diffuser baffle and a connection, provided with a filter, to atmospheric air.

A control system may be provided to operate the pulmonary dosing system in accordance with operator inputs selecting the number of patient breaths between pulses, the pulse length, and the number of pulses required to provide the prescribed amount of material to be dispensed to the patient. The exhaust filter and the apparatus for providing pulsed amounts of the therapeutically active material may be enclosed in a containment case. The dosing system is capable of supplying at least one non-toxic drug, or at least one toxic drug to the patient.

BRIEF DESCRIPTION OF THE DRAWINGS

FIG. 2 is a plan view illustrating the inhalation and exhalation elements of the system of the present invention;

FIG. 3 is a fragmentary elevational view showing the nebulizer and the plenum chamber of the present invention;

DETAILED DESCRIPTION OF THE INVENTION

Throughout this specification the word "drug" is used. This word should be interpreted to include any appropriate respirable, therapeutically active material or diagnostic agent, such as technetium-99m-labeled dimethylenetriamine pentaacetic acid (Tc 99 DTPA).

For purposes of an exemplary showing, the invention will be described in an embodiment for dispensing chemotherapy drugs. While the invention is particularly useful with toxic drugs, it is by no means intended to be so limited. Again, the invention is capable of dispensing any appropriate respirable therapeutically active material or diagnostic agent.

The drug dispensed can be a solid, a liquid or a gas aerosolized from a suspension, solution or emulsion. For example, a dry powder inhaler could be used as the apparatus for providing a pulse of respirable therapeutically active material (i.e. the powder). A solid drug could be dissolved or suspended in a liquid carrier and aerosolized. A gaseous drug can also be delivered. A liquid drug can be comminuted or aerosolized in any conventional manner, for example, using pneumatic, electrostatic or ultrasonic devices, as are well known in the art.

Figure 1:
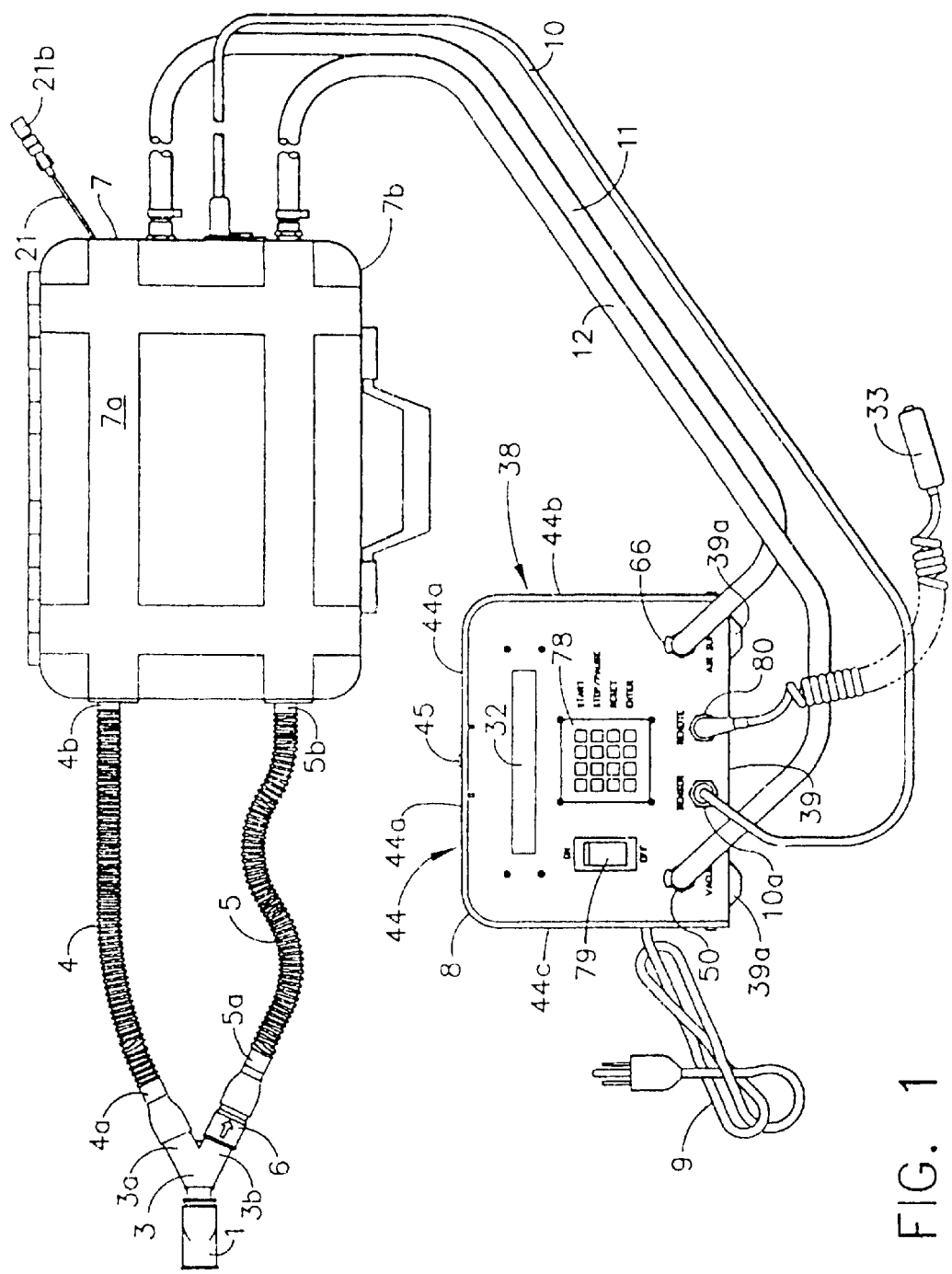
FIG. 1 is a simplified representation of the pulmonary dosing system of the present invention.

In the Figures, like parts have been given like index numerals. Reference is first made to FIG. 1 which illustrates the overall structure of the pulmonary dosing system of the present invention. The system includes a patient mouthpiece 1 to assist in containment of the aerosolized drug. The mouthpiece 1 may have, associated therewith, a mask 2, serving as an additional drug containment device. The mask is provided with a filter 2a through which air would pass should the patient cough. The filter 2a would trap aerosolized drug. The outlet of the filter 2a may lead directly to the ambient air, or it may be connected to the exhaust portion of the pulmonary dosing system.

The mouthpiece 1 is attached to a Y-adapter 3, having divergent legs 3a and 3b. An inhalation tube 4 is provided with an end 4a connected to the Y-adapter leg 3a. Similarly, an exhalation tube 5 has an end 5a connected to a check valve 6. The check valve 6, in turn, is connected to the leg 3b of Y-adapter 3. The purpose of the check valve is to assure that the patient will receive, via mouthpiece 1, only air and aerosolized drug from inhalation tube 4. It will be understood by one skilled in the art that the mouthpiece 1 could be replaced by an endotracheal tube (not shown), as is well known in the art.

When a mask is used, it will be provided with an inhalation tube and an exhalation tube joined to the mask. This may be accomplished, for example, by a mouthpiece in a manner similar to that illustrated in FIG. 2. The mask will surround the nose and mouth area of the user's face. Alternatively, a mouthpiece and nose clip combination can be used. The nose clip prevents exhalation of drug through the patient's nose.

Figure 4:
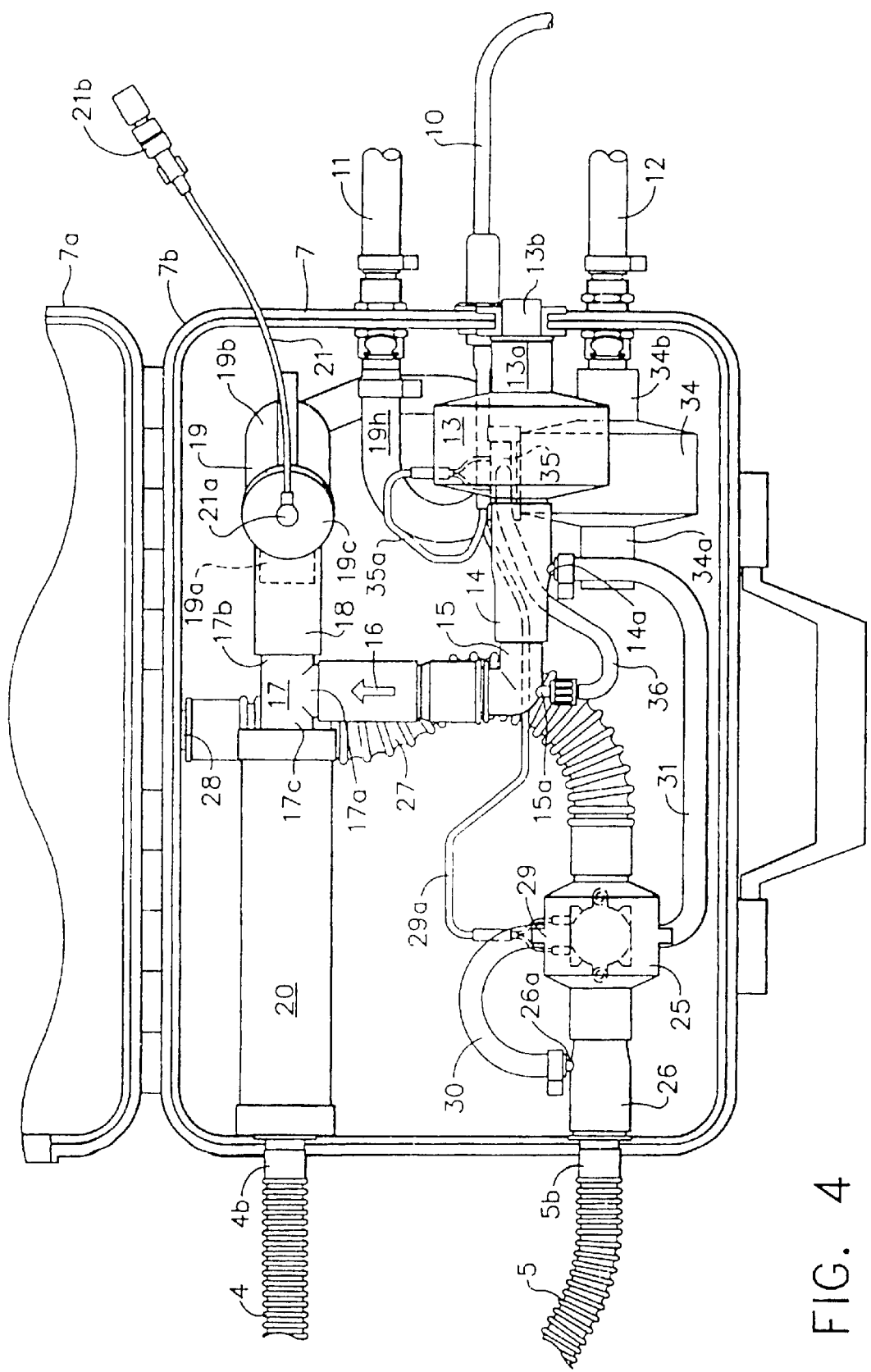
FIG. 4 is a plan view illustrating most of the inhalation and exhalation elements located in a containment case.

End 4b of inhalation tube 4 and end 5b of exhalation tube 5 are connected to adapters which pass in sealed fashion through ports in one end of a containment case 7, having a body 7a and a lid 7b (see FIG. 4). The lengths of inhalation tube 4 and exhalation tube 5 should be such as to allow a patient to sit or lie comfortably in close proximity to containment case 7.

Containment case 7 has therein a filter and an exhaust port connected to exhalation line 5. Containment box 7 also has an ambient air inlet port and filter in conjunction with a nebulizer and a plenum chamber to provide the inhalation line 4 and mouthpiece 5 with ambient air containing an aerosolized drug. All of these elements will be described in detail hereinafter.

Finally, the pulmonary dosing system of the present invention is provided with a control unit 8 connectable by power cord 9 to a source of electricity of standard hospital voltage (i.e. 115 volts, 15 amps and 60 cycles). The control unit 8 is connected to the containment case 7 by a sensor output cable 10, a pulsed air line 11 and a vacuum line 12, to be described in detail hereinafter.

Reference is now made to FIG. 2 which illustrates the inhalation and exhalation elements located within containment case 7. An inspired air filter 13 has an inlet 13a connected to a fitting 13b which passes through the containment case 7 in sealed fashion and forms an inlet port for ambient air (see also FIG. 4). The filter 13 is a standard HME filter capable of removing viruses, bacteria, etc. It will be remembered that the pulmonary dosing system of the present invention does not include a respirator or the like, and is intended for use with patients who can breathe normally.

Filter 13 has an outlet 13c adapted to receive a connector 14. The connector 14 leads to an elbow connector 15 which, in turn, leads to a check valve indicated by arrow 16. Check valve 16 is connected to the center port 17a of a T-connector 17. Another port 17b of T-connector 17 is connected by fitting 18 to the outlet 19a of an apparatus for providing a pulse of respirable drug, in this example a nebulizer 19. The third port 17c of T-fitting 17 is connected to a plenum chamber 20. The end 4b of inhalation tube 4 is connected by appropriate fitting means to the other end of plenum chamber 20, through an opening in the side wall of the containment case 7 in sealed fashion. The plenum chamber 20 will generally be oriented horizontally.

Figure 10:
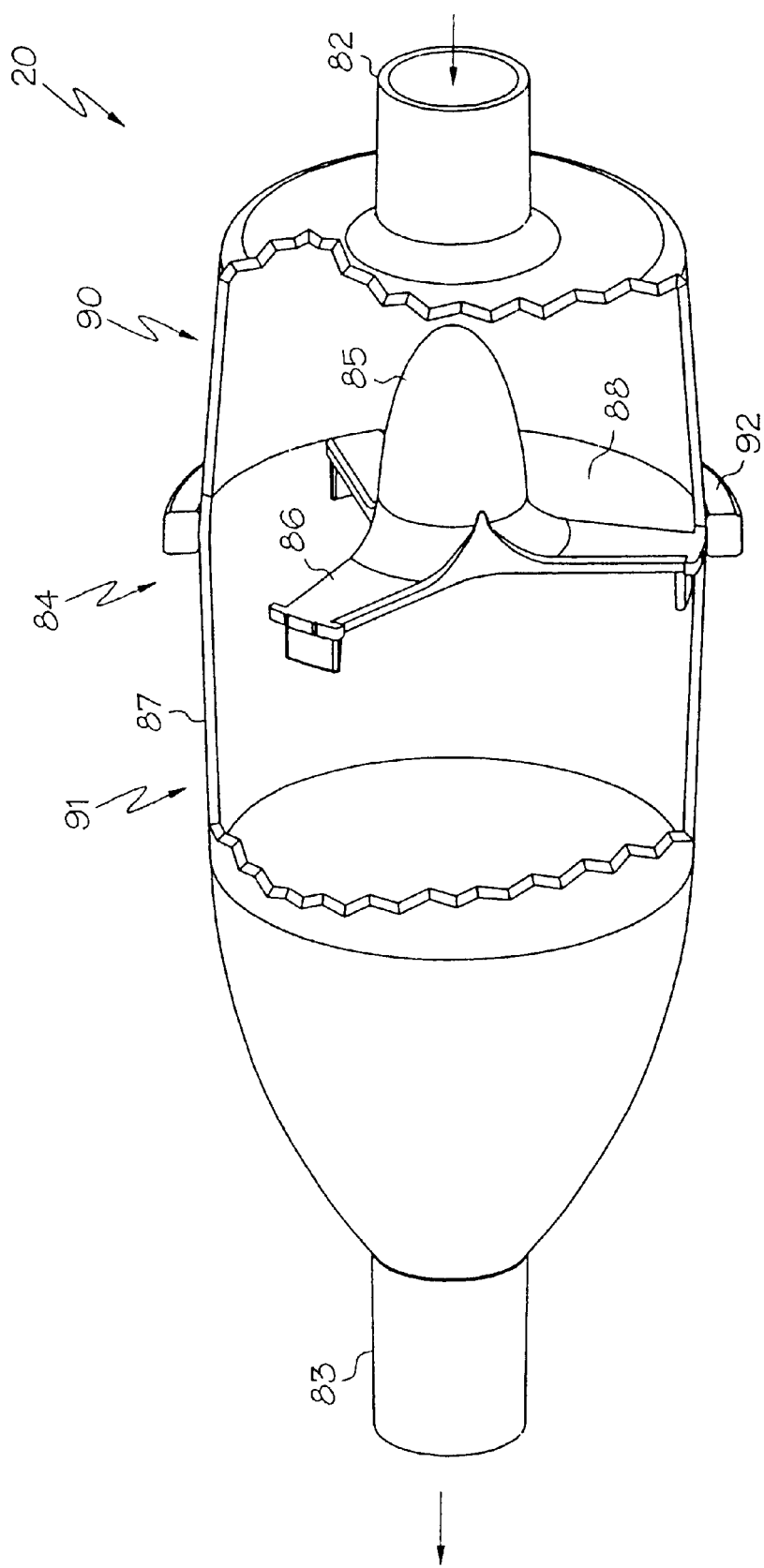
FIG. 10 is a perspective view of a plenum chamber useful in accordance with the present invention.

As shown in FIG. 10, in accordance with a specific embodiment of the present invention, plenum chamber 20 includes an inlet 82 for receiving aerosolized doses of drug from nebulizer 19 through port 17c of T-connector 17, an outlet 83 for connection to end 4b of inhalation tube 4, wherein the inlet 82 and outlet 83 are positioned along a common axis in plenum chamber 20, and a diffuser baffle 84 positioned along that axis and interposed between the inlet 82 and outlet 83.

In accordance with the embodiment shown in FIG. 10, the diffuser baffle 84 comprises a conical central portion 85 and a plurality of spokes 86 extending radially outward to wall 87 of the plenum 20 forming a plurality of passageways 88. The apex of the conical central portion 85 is positioned toward the inlet 82 such that the flow of gas constituting the aerosolized dose impacts the cone and is diverted from the axial path between inlet 82 and outlet 83 to flow through passageways 88 thereby slowing flow of the aerosolized dose and utilizing more of the available volume in plenum chamber 20. Thus the presence of the diffuser baffle 84 prevents the loss of expensive drug frequently associated with direct axial flow through the plenum chamber 20. Furthermore, the diffuser baffle 84 increases the effective useful capacity of the plenum chamber 20 by utilizing the available volume in the chamber to hold the aerosolized dose until the start of the inhalation cycle. The diffuser baffle 84 disrupts the axial flow of the aerosolized dose and utilizes the available volume in the plenum chamber 20 without resorting to vortical flow patterns which can cause undesirable drug loss caused by deposition on the chamber walls. The plenum chamber 20 may include additional diffuser baffles 84 to further disrupt the axial flow of the aerosolized dose and increase the effective utilization of the volume of the plenum chamber.

In this particular embodiment, the plenum chamber 20 comprises a first portion 90 adjacent the inlet 82 and a second portion 91 adjacent the outlet 83. First portion 90 and second portion 91 are integrally connected via an annular flange 92. Diffuser baffle 84 is interposed between the first portion 90 and the second portion 91 with the plurality of spokes 86 extending radially to engage the annular flange 92.

Although the diffuser baffle 84 is described as being conical in accordance with one embodiment of the present invention, it should be apparent to those skilled in the art that other geometric configurations will also be useful. By way of example, other designs for the diffuser baffle include cylinders, plates, circular discs, spheres, perforated plates, and the like. The specific design of the diffuser baffle is not particularly critical providing the baffle disrupts at least a portion of the axial flow of the aerosolized dose thereby utilizing more of the available volume of the plenum chamber and holding the dose in the chamber and the inhale tube until the patient inhales. The diffuser baffle may simply comprise at least one impact portion which diverts flow of the aerosolized active material and at least one non-impact portion through which the aerosolized active material flows after contacting the impact portion and being diverted from the axial path between the inlet and outlet of the plenum. Of course, the design of the impact and non-impact portions of the baffle can be optimized for a particular chamber and aerosolized dose to maximize the efficiency of the dosing process.

As illustrated in FIG. 10, the inlet 82 and outlet 83 of plenum chamber 20, although not limited to any configuration, are typically cylindrical. In accordance with certain embodiments of the present invention, the impact portion of the diffuser baffle includes at least one cross section perpendicular to the common axis of the inlet and outlet of the plenum which is greater than or equal to the cross sectional area of the inlet. This ensures that a significant portion of the aerosolized dose entering the plenum chamber through the inlet comes into contact with a solid impact portion of the diffuser baffle and is diverted from following the axial path to the outlet of the plenum. In this regard, the cross sectional area for the impact portion corresponds to the area of the solid regions of the baffle for a particular cross section, while the cross sectional area of the inlet corresponds to the area of the open regions of the inlet through which the aerosolized dose flows.

Reference is now made to FIG. 3 wherein the nebulizer 19, the T-fitting 17 and the plenum chamber 20 are more clearly shown. The nebulizer 19 has a cylindrical body 19b from which the outlet 19a extends. At its upper end, the nebulizer body 19b has top 19c which is fixedly sealed in place by an appropriate adhesive such as a silicone sealant. Top 19c has a central bore 19d into which one end 21a of an extension set 21 is fixed and sealed with an appropriate adhesive. The other end of extension set 21 is provided with a valve port 21b for the receipt of drug from a syringe pump, a hand syringe, or the like. Thus, the extension set 21 is the means by which medicine is introduced into nebulizer 19. Other means may be used, if desired.

The nebulizer bottom 19e slopes downwardly and inwardly to an integral, tube-like inlet 19f. The conical bottom 19e and tube-like inlet 19f are surrounded by a cylindrical skirt 19g comprising an integral, one-piece part of the nebulizer body 19b. One end of a tube 19h is attached to an elbow connector 22 by a tubing clamp 23. The elbow connector 22, in turn, is connected to nebulizer inlet 19f, again by a tubing clamp 24. The free end of tube 19h is attached through the end of containment case 7 to the pulsed air line 11 (see FIG. 4).

As previously stated above with respect to FIG. 2, the outlet 19a of nebulizer 19 is attached to port 17b of T-fitting 17 by connector 18 (see FIG. 4). Port 17c of T-connector 17 is attached to one end of plenum chamber 20. The end 4b of inhalation tube 4 is attached to the other end of plenum chamber 20 via an appropriate fitting. The drugs or diagnostic agents can also be introduced into the nebulizer by use of a syringe, cannula, or direct attachment of the drug container to the nebulizer.

The nebulizer 19 is made of materials which conform to biocompatibility standards ISO 10993. If chemotherapy drugs are used, the nebulizer 19 should be able to withstand exposure to such drugs. The nebulizer 19 is preferably capable of atomizing such drugs to a particle size distribution of 1 to 5 microns, with an output volume of 0.1 to 1.0 milliliter per minute.

In the embodiment being described, fitting 21b at the free end of extension set 21 may be connected to a syringe pump (not shown). The syringe pump, in conjunction with the extension set 21, provides a closed, needleless delivery system by which the chemotherapy drugs can be transferred easily and safely into nebulizer 19. This closed system should be able to withstand 54 plus 10% psi back pressure during operation. The air pulses to the nebulizer from the pulsed air system are at 54 psi and the additional 10% back pressure constitutes a safety margin.

As indicated above, in the embodiment described, delivering a toxic drug, the patient interface for the drug nebulizer should be either an endotracheal tube or a mouthpiece, preferably with a nose clip.

Depending on the nature of the drug being dispensed (i.e. toxic, non-toxic, etc.) the patient interface may comprise a plain mask, a plain mouthpiece, a mouthpiece and nose clip combination, a mask and mouth tube combination, an endotracheal tube, a nasal tube, a tent or a small room.

As is clearly shown in FIG. 2, the end 5*b* of exhalation tube 5 is connected to a fitting which passes through the end of containment case 7 in a sealed fashion and is joined to the inlet of a filter 25 by a connector 26. The filter 25 is similar to filter 13, constituting a standard HME filter. The outlet of filter 25 is connected to a non-collapsible flexible tube 27. Tube 27 terminates in an adapter 28 which passes in sealed fashion through a side wall of the containment case 7, providing an outlet for the filtered exhaled air.

Mounted on filter 25 there is a sensor switch 29. Sensor switch 29 is connected by a tube 30 to a lateral outlet 26*a* of fitting 26. In similar fashion, the sensor switch 29 is connected by a tube 31 to a lateral outlet 14*a* of connector 14 attached to filter 13. Tube 31 will contain air at ambient pressure. Tube 30 will contain air at a slightly higher pressure during exhalation by the patient. Sensor switch 29 has an output 29*a* (see FIG. 4) which becomes part of the sensor output cable 10 of FIG. 1. Sensor switch 29 will send a signal to control unit 8 during some portion of each exhalation by the patient. The sensor signal could be sent to the control unit 8 at the initiation of each exhalation. The purpose of this will be apparent hereinafter. The signals from sensor switch 29 also assure that the patient is breathing properly.

In the embodiment described, flexible inhalation tube 4 and flexible exhalation tube 5, as well as Y-adapter 3 and mouth piece 1 should not leak to atmosphere outside containment case 7. With other types of drugs this requirement would be less stringent.

Air pulses from pulsed air line 11 actuate the nebulizer. It will be noted however, that the pulses do not enter the plenum chamber 20. The pulses are electronically controlled by control unit 8. The pulsed air is preferably clean and of the same components and percentages as atmospheric air. Of course, other mixtures of gases may be used for certain patients or drugs. For example, it may be desirable to have higher or lower percentages of oxygen or carbon dioxide than are present in atmospheric air.

In the exemplary embodiment described, the air flow required for nebulization ranges from 3.5 to 12.0 liters per minute. The maximum required pressure is about 60 psi. Air pressure will be regulated over the range of from about 20 psi to about 60 psi. The air pressure will be set upon assembly of the pulmonary dosing system. These parameters may vary depending on the circumstances and the drug being dispensed.

For some therapies it is useful that the drug aerosol reaches the deep lung. The entire volume of each breath is called the "inspired volume". This inspired volume can be a normal breath, referred to as "tidal volume", or could be a deep breath of much greater volume, referred to as a "vital capacity" breath. With cooperation from the patient (in drawing a deep breath), the device enables this deep penetration by providing that the metered volume of drug aerosol from the plenum forms the first part of each inhaled breath and is followed by a volume of air which makes up the latter part of each inhaled breath (the remainder of the vital capacity). It has been determined that this air portion in the latter part of each breath tends to help push the initial drug portion down into the deep lung. If the drug made up most of the entire breath, then the latter part of each breath would not be delivered to the deep lung and may not be available for maximum benefit.

In accordance with a particular aspect of the present invention, the plenum is provided during the exhalation phase with a drug aerosol volume of about 500 cc which is equal to about ¼ to ⅛ of the amount of air a patient inhales during a typical deep breath. This volume is then inhaled in the first part of a breath followed by the air component in the latter part of the breath. The tidal volume and vital capacity may be determined by known pulmonary function tests. The control system is then programmed to deliver the selected amount of drug aerosol to the plenum based on the pulmonary function of the animal or human. Alternatively, the amount of aerosol to be inhaled may be determined by administering Tc 99 DTPA using the device.

The air supply from line 11 and line 19*h* to nebulizer 19 will be pulsed in a cycle synchronous with the patient's exhaled breath. Sensing of the patient's breathing cycle can be determined automatically or manually by a human operator. In accordance with the automatic sensing operation, sensor switch 29 (a pressure switch) will sense some part of the exhalation process. The signal from sensor switch 29 will cause a solenoid valve (to be described hereinafter) on the compressed air supply to open to nebulizer 19 for a preset pulse width. In the example described above, this sequence will occur at each exhalation.

In some instances it is desirable to provide the drug in a more relaxed manner, providing for one or more exhalations between pulses to the nebulizer. The number of exhalations between air pulses will depend upon the patient, the patient's breathing capacity, and the like. As an example, for a given patient, the control unit may be set for three or more exhalations between air pulses. Under this circumstance, the patient's first breath after a pulse would constitute mostly drug. The patient's second breath would also be mostly air and some residual drug. The third breath would be substantially air. Upon the initiation of the third exhalation, an air pulse would occur. Such a cycle is continuously repeated while the drug is being delivered and this is continued for a set number of breaths.

The total number of breaths required to deliver the drug can be calculated. The total dose of drug can be delivered as determined by a set number of breaths based on the calculated drug dose per breath. The control unit 8 (see FIG. 1) is provided with a liquid crystal display 32, visible to the patient, that will count down the number of breaths required to consume the drug dose. Control unit 8 is also provided with a reset button in case the drug is not completely consumed in the allocated number of breaths. Similarly, the control unit is provided with a remote on-off switch 33 enabling the patient or an operator to stop and restart a cycle should the patient feel either distressed or the need for a few more breaths before the next pulse.

The effective drug dosage for particular patient may vary. A method for using the inventive device for determination of an effective drug dosage is described in U.S. Pat. No. 6,269,810.

The results of the described test method are then used to calculate the number of dosing breaths needed, and optionally the corrections to the inhalation device to deliver the predetermined dose to the patient in the subsequent administration step. Corrections to the device, if used, typically include resetting the aerosol generation time, the delay time between activation of the nebulizer and aerosolization, pressure used to drive the nebulizer, amount of drug placed in the device, adjustment of the device to obtain a different particle size, and so on. The patient breathes from the inhalation device used for the tests, or a substantially similar device, for the calculated number of dosage breaths.

Based on the information obtained during the test phase, one can determine the amount of drug to be aerosolized, inhalation device settings needed to obtain the required amount of aerosolized drug to be administered to the patient and the required number of dosage breaths needed to administer the predetermined dose of drug to the patient.

It will be understood by one skilled in the art that the pulse sequence can be manipulated in any number of ways to change the rate of drug delivery over time. For example, the drug quantity can be ramped up or ramped down over time, or otherwise set at whatever quantity versus time is desired.

The amount/timing of drug delivery could also be altered based on feedback data from the patient. Spirometry data (such as tidal volume, vital capacity, inhalation rate, etc.) or physiological data in the exhaled breath (such as residual drug content, blood gases, mass balance) could be monitored to calculate and adjust new delivery profiles. Biosensors (such as EKG, glucose and pulse sensors) could be used to measure body functions or responses to the drug to provide feedback that is used to customize the delivery profile and optimize mass transfer of drug.

It is also to be understood that the amount/timing of drug delivery does not have to be accomplished automatically in the present invention. The drug can be dosed manually, for example by a nurse activating a trigger mechanism, based on the breathing cycle of the patient.

As indicated above, chemotherapy drugs may have certain serious toxic effects. It is therefore imperative that such a drug be contained. Containment of any fugitive aerosolized drug must be assured. This is accomplished, in part, by the provision of containment case 7 and by maintaining a negative pressure (vacuum) within the containment case. The lid 7a of containment case 7, when closed, makes a seal with the containment case body 7b. Alternatively, an active flow system may be utilized to ensure proper flow of the aerosolized dose through the device. Other factors involved in containing the aerosolized drug include using a pulsed aerosolization system instead of a continuous one and maintaining a closed breathing circuit. These requirements are not as important when delivering a drug without the associated toxic effects.

Figure 5:
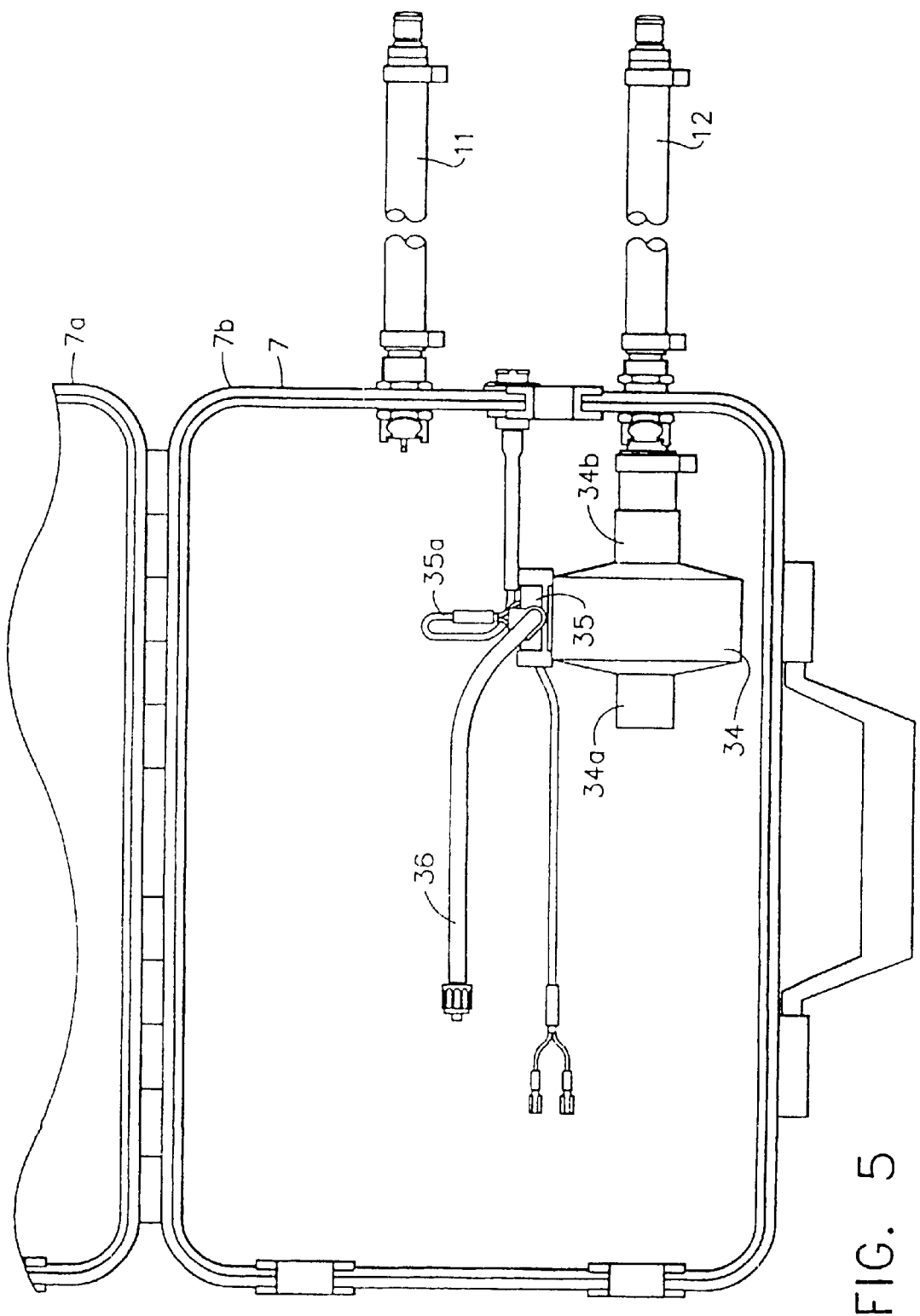
FIG. 5 is a fragmentary plan view illustrating the vacuum components of the present invention located within the containment case.

Reference is now made both to FIGS. 4 and 5. A filter 34, similar to filters 13 and 25, is located within containment case 7. The filter 34 has an inlet 34a open to the interior of containment case 7. Filter 34 has an outlet 34b provided with an appropriate adapter to enable it to be connected to vacuum line 12, in a sealed fashion through the end wall of containment case 7. Vacuum line 12 is connected to a vacuum pump within control unit 8, as will be explained hereinafter.

Filter 34 has mounted thereon a vacuum sensor switch. The sensor switch 35 is connected by a tube 36 to a lateral outlet 15a of elbow connector 15. Sensor switch 35 senses the presence of a vacuum within containment case 7 and has an output 35a connected to the sensor output cable 10 (see FIG. 1) to control unit 8. Should there be a loss of vacuum, control unit 8 will turn off the air pulse compressor to the nebulizer.

Filter 13, 25 and 35 are all described as constituting standard HME filters. In fact, these filters could be any devices for removing toxic materials. Absorbers (such as activated charcoal) or physical separators (such as electrostatic precipitators) could be used.

The interior of containment case 7 should be easy to clean. All interior surfaces should be smooth and without crevices. After each use, the entire contents of containment case 7 (except vacuum filter 34 and vacuum sensor 35), together with inhalation tube 4, exhalation tube 5, Y-fitting 3, mouth piece 1 and mask 2 may be disposed of. FIG. 4 illustrates the arrangement of the various elements within the containment case 7. In FIG. 5, everything has been removed from the containment case 7 except for the vacuum filter and vacuum sensor which are partially obscured in FIG. 4.

Figure 6:
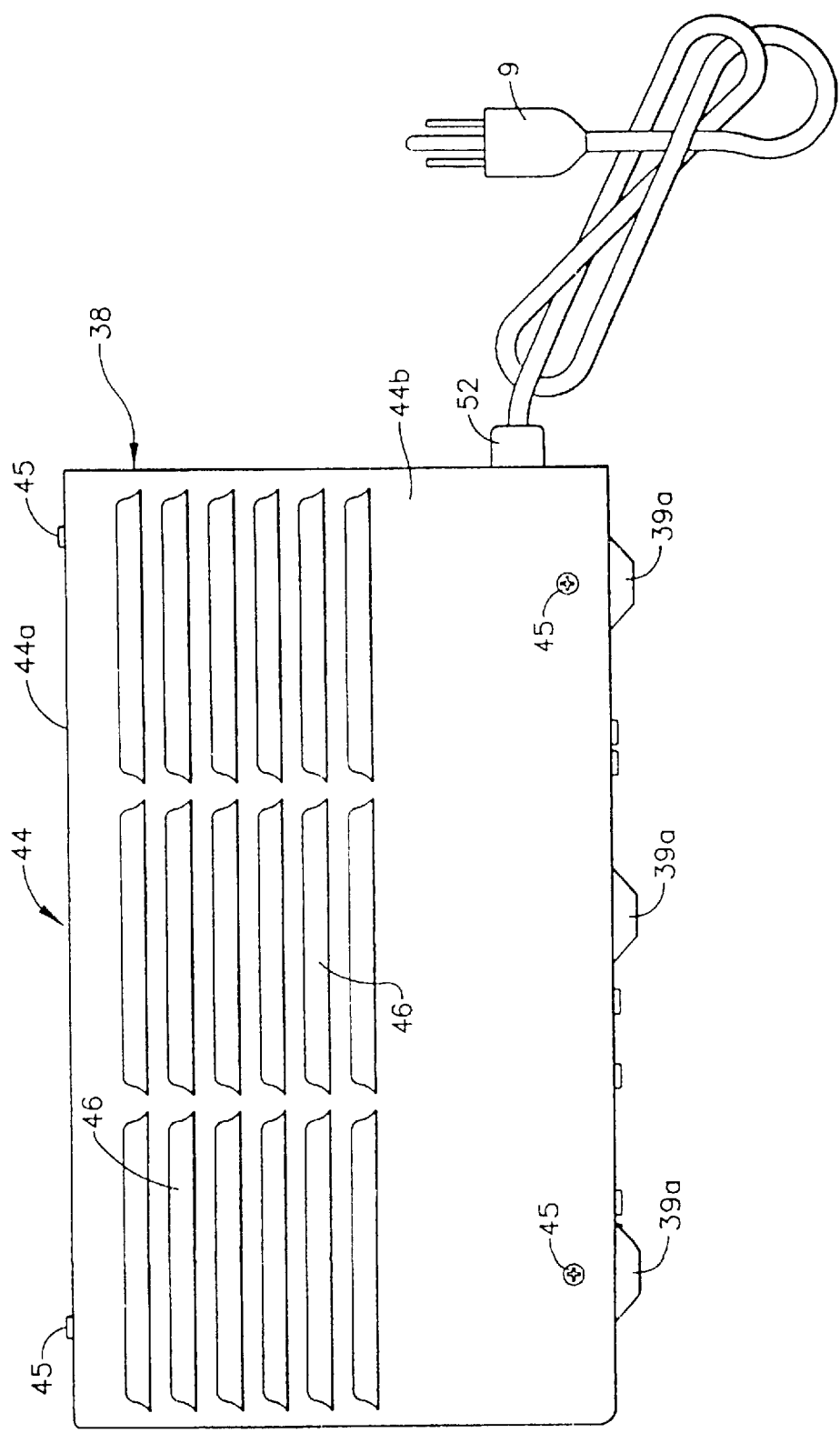
FIG. 6 is a side elevational view of the control assembly of the present invention.
Figure 7:
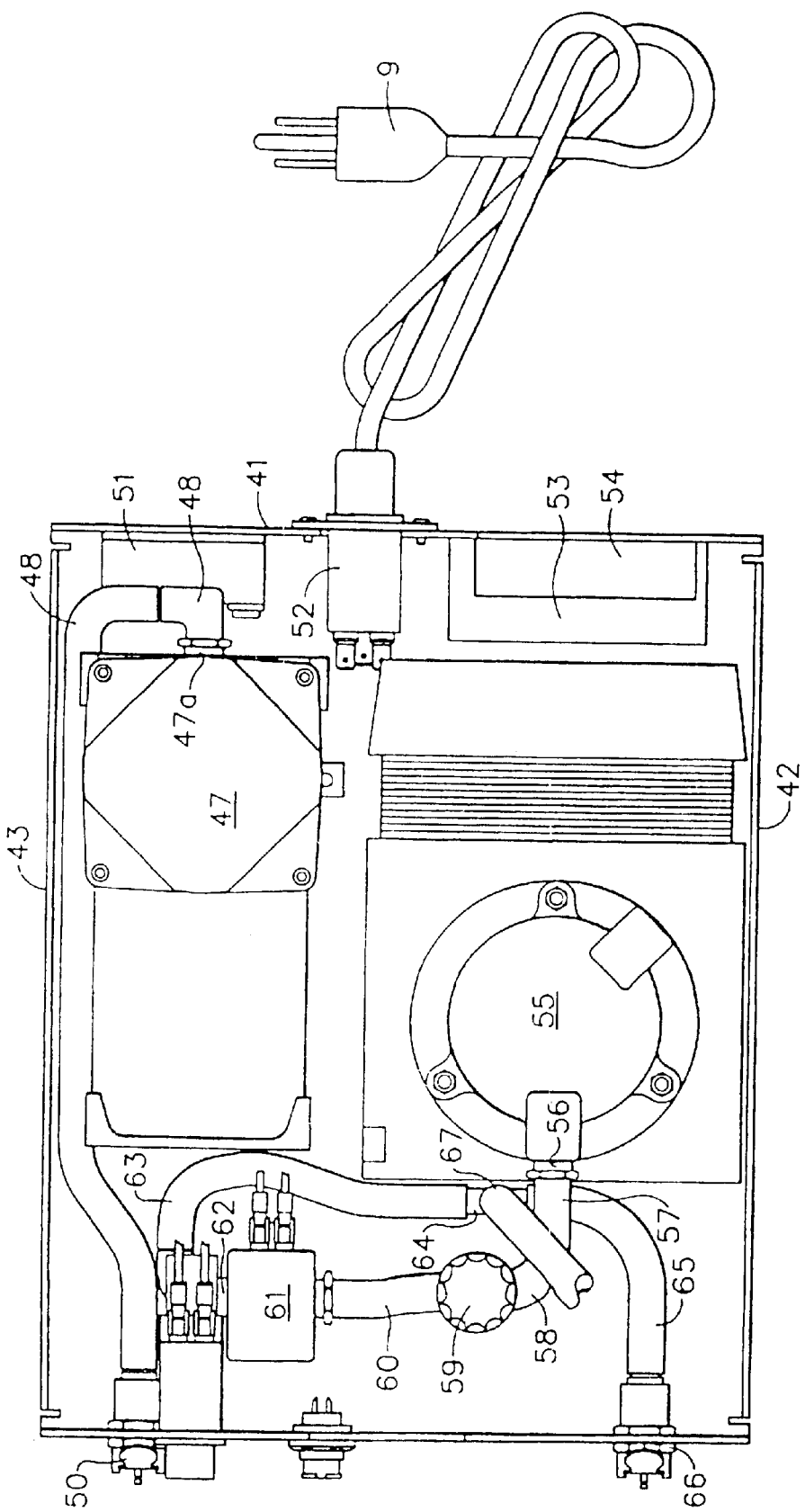
FIG. 7 is a plan view of the control assembly with its outer casing removed, together with the upper layer of the components.
Figure 8:
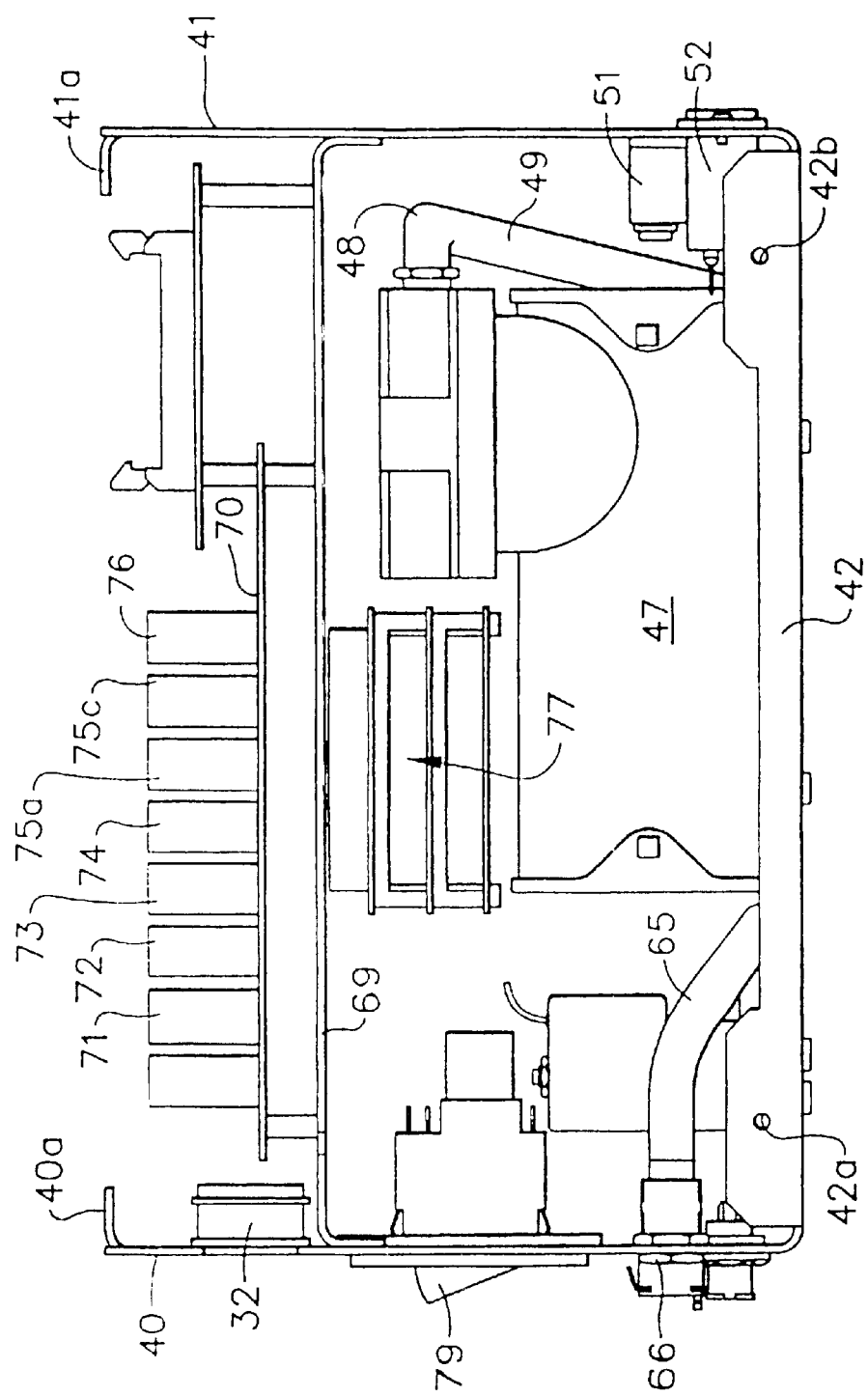
FIG. 8 is a side elevational view of the control assembly with the outer casing and the compressor removed.
Figure 9:
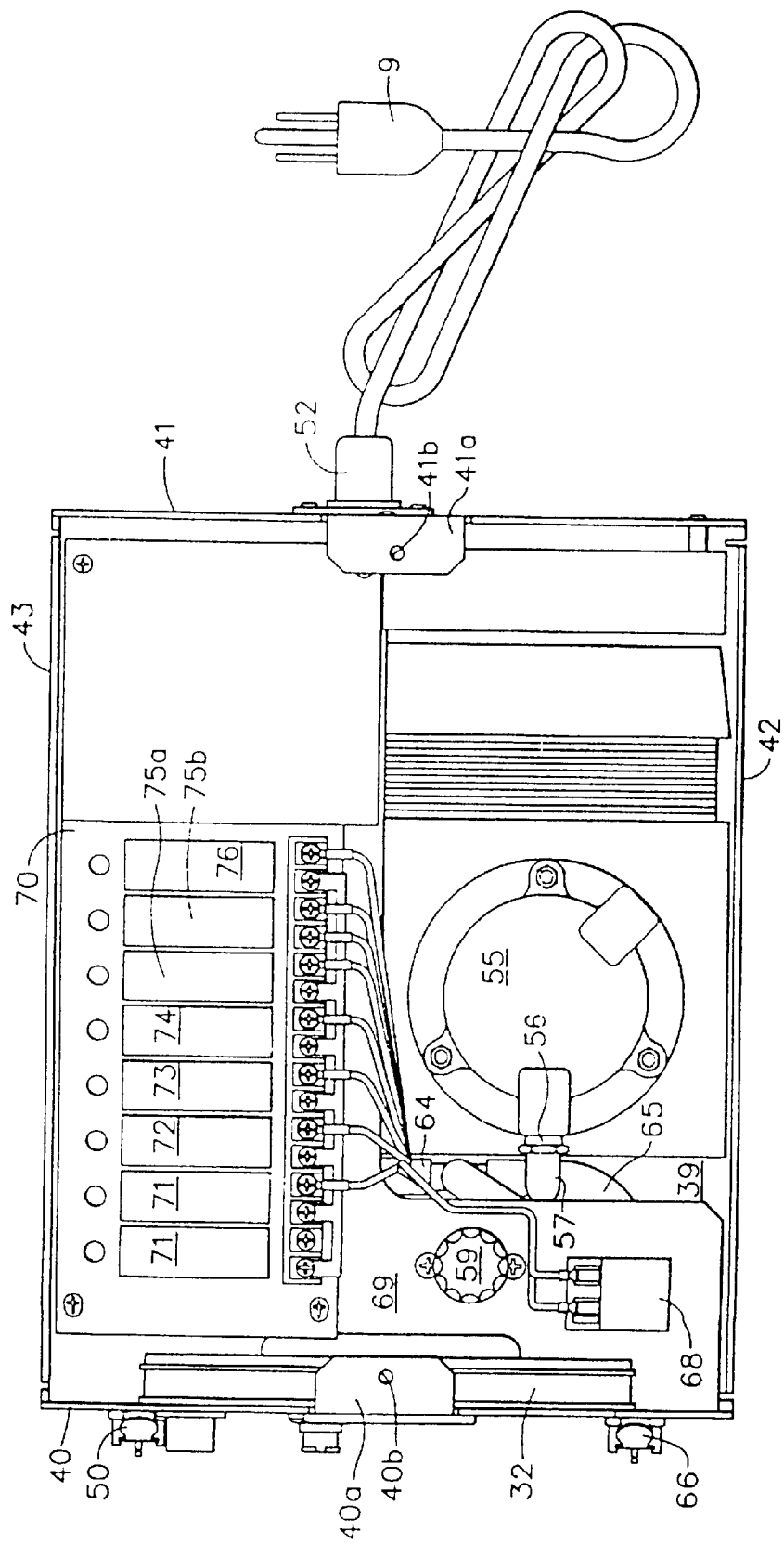
FIG. 9 is a plan view of the control assembly with the outer casing thereof removed.

Reference is now made to FIGS. 1 and 6–9 in which the control unit 8 is illustrated. Control unit 8 has a housing generally indicated at 38. As is best shown in FIGS. 8 and 9, the housing comprises a bottom panel 39 with upturned front and rear end panels 40 and 41, respectively. Bottom panel 39 has, along each of its longitudinal edges, an upstanding flange. These flanges are shown at 42 and 43. Flange 42 is provided near its ends with threaded perforations 42a and 42b. Longitudinal flange 43 will be provided with similar threaded perforations (not shown). Front panel 40 has along its upper edge an integral in-turned tab 40a. The tab 40a has a threaded perforation 40b formed therethrough (see FIGS. 7 and 9). In a similar fashion, the rear panel 41 is provided with an in-turned tab 41a, centered with respect to its upper edge. The tab 41a has a threaded perforation 41b extending therethrough. The housing 38 is completed by a U-shaped outer casing generally indicated at 44 and comprising the top 44a and sides 44b and 44c of control unit 8. As is shown in FIGS. 1 and 6, the side 44b of control unit 8 is attached to the longitudinal flange 42 by means of screws 45 threadably engaged in flange perforations 42a and 42b (see FIG. 8). It is within the scope of the invention to provide side 44b with a plurality of louvers to allow for cooling of the contents of housing 38. Side wall 44c may be identical to side wall 44b and may be attached to longitudinal flange 43 (see FIG. 7) in an identical manner. The top 44a is attached to in-turned flanges 40a and 41a of the front and rear panels, respectively by means of additional screws 45, as shown in FIGS. 1 and 6. The bottom panel is provided with depressions 39a serving as feet for the control unit 8, and allowing air circulation around the control unit.

Reference is made to FIGS. 7 and 8 which illustrate a vacuum pump 47. Vacuum pump 47 has an outlet 47a to which an elbow hose barb 48 is connected. Hose 49 is connected to elbow 48 and extends to the forward panel 40 of control unit 8, where it is attached to a vacuum connector 50 which extends through front panel 40. Vacuum connector 50 is adapted to receive the free end of vacuum hose 12. As is shown in FIG. 7, immediately behind vacuum pump 47 there is a solid state relay 51 which turns the vacuum pump 47 on and off in a response to a signal from the computer (to be described hereinafter).

Centered on the back panel 41, near its bottom edge, there is a connector 52 for power cord 9. Elements 53 and 54, adjacent rear wall 41 constitute 12 V and 5 V DC power supplies.

To supply the pulsed air for nebulizer 19, control unit 8 contains a compressor. While the compressor has been removed from FIG. 8 so that other elements could be seen, it is shown in FIGS. 7 and 9 at 55. The compressor 55 has an outlet 56 which is connected by means of an elbow fitting 57 to a tube 58. As is shown in FIG. 7, tube 58 is connected to a pressure regulator 59. Regulator 59, in turn, is connected by a tube 60 to the inlet of a pulse generating electric air valve 61. The outlet of the pulse generating electric air valve is provided with an elbow 62, connected to a tube 63. Tube 63 is connected to one port of a T-fitting 64. Another port of T-fitting 64 is connected by tube 65 to a fitting 66 which extends through front panel 40 of control unit 8. Pulsed air line 11 attaches to fitting 66 (see FIG. 1). The intermediate port of T-fitting 64 is connected by a tube 67 to a pressure sensing safety switch 68. Safety switch 68 assures proper pressure from compressor 55. It will also cause the compressor to be shut down should there be a gross hose or fitting leak.

Turning to FIGS. 8 and 9, the front and rear ends 40 and 41, support an L-shaped shelf 69. Mounted on shelf 69 there is an 8-position single channel I/O board 70. The board 70 serves as an interface between the computer (to be described) and various sensors of the pulmonary dosing system. Attached to the I/O board 70, there are a number of DC input modules 71–74. There are also DC output modules 75*a* and 75*b*, together with an AC output module 76.

Just below shelf 69 there is a module generally indicated at 77 which comprises an embedded computer, a keypad and LCD interface board, and a signal conditioning interface.

Turning to FIG. 1, the forward face of control unit 8 has the liquid crystal display 32, mentioned above. In addition, there is a keypad 78 providing an interface between the operator and the computer. The overall control unit has a main on/off switch 79 and the vacuum connection 50, the pulsed air connection 66, the remote switch connection 80 to receive the connector end of manual switch 33 by which the patient or operator can introduce a pause in the dosing cycle. Finally, the control unit has a connector 10*a* for sensor cable 10 which contains the outputs of exhalation sensor switch 29 (see FIG. 2) and vacuum sensor switch 35.

The use of compressor 55 to provide the pulsed air for nebulizer 19 is preferred, because it renders the overall pulmonary dosing system a self-contained system. There is no need to provide an air tank, or to rely on air supplied by a hospital, a clinic or the like, although these may be used.

From the above description it will be noted that the control 8 has three operator or patient interfaces, each passing information in only one direction. The liquid crystal display 32 constitutes a user interface and will allow the control system to communicate with the operator and the patient, prompting the operator for inputs and conveying information to the patient or the operator during operation of the pulmonary dosing system. Keypad 78 is an operator interface and allows the operator to enter numeric data into the system. Furthermore, the keypad will enable the operator to enter system commands (such as START, PAUSE/STOP, and RESET) by means of dedicated keys on the keypad. Keypad 78 will also have an enter key enabling the operator to instruct the control unit 8 to accept data entered by means of the keypad.

Remote switch 33 is used to indicate when to start or pause the operation of the pulmonary dosing system. Control unit 8 is provided with a built-in beeper or alarm which is sounded every time the remote switch is actuated. The remote switch may be actuated by either a qualified operator or the patient. A trained operator should be present at all times during operation of the pulmonary dosing system. It is not to be operated in an unattended mode. Since, in the embodiment described, the drugs being delivered by the pulmonary dosing system are highly toxic, both the system and its software are designed and constructed to minimize the safety hazard posed by the drugs. It will be assumed that the pulmonary dosing system will be powered down any time drugs are loaded into the nebulizer 19, or the lid 7*a* of containment box 7 is open. In the embodiment described, the patient and the pulmonary delivery system must be enclosed in a negative pressure tent with a HEPA filter as a secondary system to contain aerosolized drug in the event that the patient coughs or removes the mouthpiece prior to exhaling. The operator should not press on/off switch 79 or remote switch 33 unless the patient has the mouthpiece in place in his mouth.

It will be understood that with respect to hardware interfaces, the system will have a dedicated interface to keypad 78, a dedicated interface to liquid crystal display 32, a dedicated interface to the beeper or alarm, and a discrete input/output interface to the rest of the control unit elements. This interface is used by the computer to actuate the mechanical components of the pulmonary delivery system.

The software for controller 77 will perform the following functions: it will allow the operator to set up the system for a particular patient and the hardware being used; it will notify the operator when any of the exception modes (pause, reset, or set up mode) are detected; it will operate the system in a consistent manner; and it will notify the operator when any of the alarm conditions (loss of breath, loss of vacuum, loss air pressure, no breath, long breath, vacuum sensor switch closed, and pressure sensor switch closed) is detected. It will allow the operator to set the time of nebulizer air pulse width, based upon the drug being delivered. It will allow the operator to set the amount of exhales between air pulses based upon the patient to whom the drug is being delivered. When the air compressor has been turned off, the software will see that the vacuum pump will be left on, to assure complete evacuation of any aerosolized drug. When a loss of vacuum is detected, the software will cause the air compressor 55 to be shut down while the vacuum pump continues to run until power is turned off. The software enables the operator to enter the dose either in terms of milliliters or number of breaths. The software will calculate the number of breaths required to empty the nebulizer 19. The software will also cause the beeper or alarm to sound if sensor 29 does not detect any breaths for 10 seconds. This will assure that the patient is breathing properly and that the patient is exhaling into the mouthpiece. The beeper or alarm will sound if there is a loss of air pressure as detected by pressure sensor switch 68, or if there is a loss of vacuum as sensed by vacuum sensor switch 35. The software also provides a number of other checks, as will be apparent hereinafter. For example, the pulmonary delivery system will not be allowed to start a cycle if the remote switch 33 is not plugged into connector 80.

Again, it is to be emphasized that in addition to the automatic dosing described herein, the present invention also encompasses manual dosing of the drug, for example by a nurse, technician or the patient activating a trigger mechanism, based on the breathing cycle of the patient.

The software operating requirements for the pulmonary delivery system may be subdivided into a number of categories.

The pulmonary dosing system having been described in detail, it will be evident that a pulmonary dosing system capable of safely administering chemotherapy drugs (as well as other drugs) is provided. The pulmonary dosing system is totally self-contained, requiring only connection to a source of electrical current. Certain parameters can be input by a skilled operator, so that the system can be tailored to a particular patient and the particular drug being administered.

Modifications may be made in the invention without departing from the spirit of it. For example, the present invention may be used in veterinary applications. Under these circumstances the patient interface or mask and the dosage delivery software would be customized.

The inlet and exhalation tubes to the mask could be concentric (coaxial). The compressor and vacuum elements could be merged into one pump and a closed system could be provided in this manner. The compressor side provides the pulsed drug to the patient. The vacuum side retrieves the drug and air from the container (as currently shown) and provides it to the compressor side. Of course, the drug is filtered out of the air as it is retrieved and recycled back to the compressor.

The containment case 7 and the control unit 8 could be joined together in one unit. However, seals would still have to be maintained to keep them chemically separate to prevent the drug and gases from getting to the control side of the package. This might be part of an effort to reduce the size of the overall package. With respect to the plenum, more than one drug could be introduced therein at the same time. The plenum could have an adjustable volume (using a bellows or piston, for example) to allow optimized delivery for different patients and different therapies.

Finally, there are a variety of known electronic solutions for controlling a system like the drug delivery device of the present invention. It could easily be controlled by a microprocessor. Other possible features of a controller for the present invention could include:

Sharing data with other devices (such as other diagnostic devices or patient databases) so that information may come from other sources than the front panel entry;

Having lockouts or other security features to control access;

Containing a modem for remote monitoring or reporting;

Being programmable to make it drug specific so that only one drug can be used (identified by bar coding or ion sensing, for example) or patient specific so that positive patient identification is required; and Being programmed to make the modifications based on feedback from sensors, as discussed above.

EXAMPLES

The following examples are offered by way of illustration, not by way of limitation.

A side-by-side aerosol test was performed to evaluate the benefit of the diffuser (i.e., invention) relative to the pulmonary drug delivery device. Two test specimens were utilized—Plenum #1 and Plenum #2. They were identical in materials, volume, and geometry except that Plenum #2 included a diffuser in accordance with the present invention enclosed within the plenum #2's interior. The test was conducted under identical conditions using the same formulation and concentration of drug product. The two test specimens shared the same aerosol generator as well. Dose uniformity (Table 1) and particle size (Table 2) distribution were measured.

The data in Table 1 indicate that a 23.7% increase in drug dose (mg) resulted by using the plenum with the diffuser (Plenum #2). Furthermore, dose uniformity for the diffuser test specimen (Plenum #2) was more consistent with less variation as compared to the prior art plenum without a diffuser. The data in Table 2 indicate that the diffuser in the plenum provides the aforementioned benefits in dosage level and uniformity without significantly affecting the aerosol's particle size.

TABLE 1

| | Dose Uniformity (mg) | | | | | | |
|---|---|---|---|---|---|---|---|
| | RUN 1 (n = 12) | | | RUN 2 (n = 10) | | | Grand |
| Test Specimen | MEAN | SD | RSD | MEAN | SD | RSD | Mean |
| Plenum 1 (w/o diffuser) Comparative | 0.169 | 0.016 | 9.368 | 0.177 | 0.009 | 5.354 | 0.173 |
| Plenum 2 (w/diffuser) | 0.212 | 0.010 | 4.627 | 0.216 | 0.007 | 3.020 | 0.214 |

TABLE 2

| | Particle Size Distribution* | |
|---|---|---|
| Test Specimen | MMAD ($\mu$m) | GSD |
| Plenum 1 (w/o diffuser) Comparative | 1.4 | 2.4 |
| Plenum 2 (w/diffuser) | 1.6 | 2.6 |

*Anderson Cascade Impactor at 28.3 L/min
Test Parameters (Tables 1 and 2 above)
Sampling flow rate = 28.3 L/min
Aerosol time = 3 sec
Sampling Time = 4 sec
MMAD = Mass Median Aerodynamic Diameter
GSD = Geometrical Standard Deviation
SD = Standard Deviation
RSD = Relative Standard Deviation
= SD/Mean × 100

What is claimed is:

1. A pulmonary dosing system for supplying a predetermined amount of a therapeutically active material to a patient, said system comprising:

an apparatus for providing an aerosolized amount of a therapeutically active material said apparatus having an outlet for conveying said aerosolized amount of active material; and a plenum chamber having an inlet for receiving said aerosolized amount of active material and an outlet for connection to a mouthpiece for delivering said aerosolized amount of active material to a patient, wherein said inlet and said outlet of said plenum chamber and said outlet of said apparatus are oriented along a common axis, and at least one diffuser baffle interposed between said inlet and said outlet of said plenum chamber wherein said diffuser baffle disrupts flow of said aerosolized amount of active material along said common axis in said plenum chamber thereby causing said aerosolized amount of active material to be retained in said chamber until inhaled by the patient.

2. The pulmonary dosing system of claim 1 wherein said aerosolized amount of a therapeutically active material is aerosolized from a solution, suspension or emulsion of said active material.

3. The pulmonary dosing system of claim 2 wherein said apparatus generates a pulsed amount of said active material in aerosolized form.

4. The pulmonary dosing system of claim 3 wherein said pulsed amount of active material is aerosolized in atmospheric air.

5. The pulmonary dosing system of claim 1 wherein said diffuser baffle comprises at least one impact portion which diverts flow of said aerosolized active material and at least one non-impact portion through which said aerosolized active material flows after impacting said impact portion.

6. The pulmonary dosing system of claim 5 wherein said inlet is cylindrical and said impact portion of said diffuser baffle includes at least one cross section perpendicular to said common axis having an area approximately equal to or greater than the cross sectional area of said inlet.

7. The pulmonary dosing system of claim 5 wherein said impact portion of said diffuser baffle comprises a conical portion having an apex proximal said inlet.

8. The pulmonary dosing system of claim 7 wherein said diffuser baffle further comprises a plurality of spokes extending radially from said conical portion.

9. The pulmonary dosing system of claim 1 wherein said plenum chamber comprises a first section including said inlet and a second section including said outlet wherein said diffuser baffle is disposed between said first and second sections of said plenum chamber.

10. The pulmonary dosing system of claim 1 wherein said therapeutic active material comprises a chemotherapy drug.

11. A pulmonary dosing system for supplying to a patient a predetermined amount of respirable therapeutically active material, said system comprising a patient interface connected to an inhalation tube and an exhalation tube, a check valve provided in association with said exhalation tube to prevent inhalation therethrough, a first filter having an inlet and an outlet, said exhalation tube being connected to said inlet of said first filter, said outlet of said first filter being in fluid communication with atmosphere, a second filter having an inlet and an outlet, with the second filter inlet in fluid communication with atmosphere and said second filter outlet having a second check valve to prevent said therapeutically active material from escaping to atmosphere, said second filter outlet being connected to said inhalation tube, an apparatus for providing pulsed amounts of said therapeutically active material aerosolized in filtered atmospheric air, a plenum chamber connected to said apparatus, said plenum chamber comprising an inlet for receiving said pulsed amounts of therapeutically active material aerosolized in filtered air and an outlet for connection to said inhalation tube wherein said inlet and said outlet of said plenum chamber are located on a common axis and said plenum chamber comprises at least one diffuser baffle positioned on said axis whereby said diffuser baffle reduces axial flow of said aerosolized active material from said inlet to said outlet of the plenum chamber, and a control unit for pulsing air to entrain said therapeutically active material in a cycle synchronous with a patient's exhalations for inhalation in conjunction with the patient's natural breathing.

12. The pulmonary dosing system claimed in claim 11 wherein said active material comprises a chemotherapy drug.

13. The pulmonary dosing system claimed in claim 11 wherein said apparatus for providing pulsed amounts of said therapeutically active material comprises a nebulizer having a first inlet connected to a source of pulsed air from said control unit, said nebulizer having a second inlet for receipt of a predetermined amount of said therapeutically active material, said nebulizer having an outlet, a T-fitting having first and second concentric ports and a third intermediate port, said nebulizer outlet being connected to said first T-fitting port, said plenum chamber inlet being connected to said T-fitting second port, said plenum chamber outlet being connected to said inhalation tube, said second filter being connected to said intermediate port of said T-fitting to supply air to said plenum chamber.

14. The pulmonary dosing system of claim 11 wherein said aerosolized amount of a therapeutically active material is aerosolized from a solution, suspension or emulsion of said active material.

15. The pulmonary dosing system of claim 11 wherein said diffuser baffle comprises at least one impact portion which diverts flow of said aerosolized active material and at least one non-impact portion through which said aerosolized active material flows after impacting said impact portion.

16. The pulmonary dosing system of claim 15 wherein said inlet is cylindrical and said impact portion of said diffuser baffle includes at least one cross section perpendicular to said common axis having an area approximately equal to or greater than the cross sectional area of said plenum chamber inlet.

17. The pulmonary dosing system of claim 15 wherein said impact portion of said diffuser baffle comprises a conical portion having an apex proximal said inlet.

18. The pulmonary dosing system of claim 17 wherein said diffuser baffle further comprises a plurality of spokes extending radially from said conical portion.

19. The pulmonary dosing system of claim 11 wherein said plenum chamber comprises a first section including said inlet and a second section including said outlet wherein said diffuser baffle is disposed between said first and second sections of said plenum chamber.

20. The pulmonary dosing system claimed in claim 17 wherein said therapeutically active material comprises a chemotherapy drug.

21. A pulmonary dosing system for delivering a drug to the lungs of a patient wherein the patient is breathing without mechanical assistance and has an established breathing cycle comprising an inhalation phase during which an inspired volume of gas is inhaled and an exhalation phase during which gas is exhaled, said system comprising:
  a) a plenum for holding aerosolized drug for inhalation as the first part of the inspired volume of gas for the inhalation phase, said plenum comprising:
    an inlet for receiving an aerosolized drug,
    an outlet for connection to a patient interface, and
    at least one diffuser baffle, wherein said at least one diffuser baffle is interposed between said inlet and said outlet to divert at least a portion of said aerosolized drug as said aerosolized drug flows from said inlet to said outlet,
  b) an aerosol-producing device for delivering aerosolized drug to the plenum,
  c) a controller for signaling the aerosol-producing device to deliver a selected volume of drug aerosol to the plenum prior to the inhalation phase of the patient,
  d) a source of air for delivering a volume of air which makes up the latter part of the inspired volume of gas for the inhalation phase, said air being drawn into the plenum through a filter with an inlet connected to ambient air and an outlet having a check valve through which said air is introduced into said plenum, and
  e) a patient interface for delivering the selected volume of drug aerosol from the plenum and the volume of air to the patient whereby the selected volume of drug aerosol that makes up the first part of the inspired volume of gas and the volume of air makes up the latter part of the inspired volume of gas for the inhalation of the patient directly following said pulse to help push the selected volume of drug aerosol making up the first part, into the lung in conjunction with the patient's natural breathing.

22. The pulmonary dosing system claimed in claim 21 wherein said inlet and said outlet of said plenum are oriented along a common axis.

23. The pulmonary dosing system claimed in claim 21 wherein said aerosol-producing device comprises a nebulizer.

24. The pulmonary dosing system claimed in claim 21 wherein said aerosolized drug is aerosolized from a solution, suspension or emulsion of said active material drug.

25. The pulmonary dosing system of claim 21 wherein said diffuser baffle comprises at least one impact portion which diverts flow of said aerosolized active material and at least one non-impact portion through which said aerosolized active material flows after impacting said impact portion.

26. The pulmonary dosing system of claim 25 wherein said inlet is cylindrical and said impact portion of said diffuser baffle includes at least one cross section perpendicular to said common axis having an area approximately equal to or greater than the cross sectional area of said inlet.

27. The pulmonary dosing system of claim 25 wherein said impact portion of said diffuser baffle comprises a conical portion having an apex proximal said inlet.

28. A method for delivering a drug to the lungs of a patient wherein the patient has an established breathing cycle comprising an inhalation phase during which an inspired volume of gas is inhaled and an exhalation phase during which gas is exhaled, comprising the steps of aerosolizing the drug to produce a selected volume of drug aerosol, and delivering the selected volume of drug aerosol to a plenum during the patient exhalation phase, said plenum comprising an inlet for receiving said drug aerosol, an outlet for connection to a patient interface, and a diffuser baffle interposed between said inlet and outlet wherein said inlet and outlet are positioned on a common axis and said diffuser baffle disrupts flow of said drug aerosol along said axis through said plenum.

29. The method of claim 28 comprising the additional steps of delivering the selected volume of drug aerosol from the plenum to the patient as the first part of the inspired volume of gas on the inhalation phase; and delivering a volume of air which makes up the latter part of the inspired volume of gas on the inhalation phase to help push the selected volume of drug aerosol, making up the first part, into the lung in conjunction with the patient's natural breathing.

30. The method for delivering a drug as claimed in claim 28 wherein said diffuser baffle comprises at least one impact portion which diverts flow of said aerosolized active material and at least one non-impact portion through which said aerosolized active material flows after impacting said impact portion.

31. The pulmonary dosing system of claim 30 wherein said inlet is cylindrical and said impact portion of said diffuser baffle includes at least one cross section perpendicular to said common axis having an area approximately equal to or greater than the cross sectional area of said inlet.

32. The pulmonary dosing system of claim 30 wherein said impact portion of said diffuser baffle comprises a conical portion having an apex proximal said inlet.

33. The method for delivering a drug as claimed in claim 28 wherein said drug is aerosolized using a nebulizer.

34. The method for delivering a drug as claimed in claim 28 wherein said drug comprises a chemotherapy drug.

35. A plenum for use in a pulmonary dosing system comprising: a first section including an inlet, a second section including an outlet and a diffuser, the first section and the second section being assembled to form a chamber in which the inlet and the outlet are oriented along a common axis, and at least one baffle interposed between the first section and the second section on the common axis so as to direct the flow of a gas as it passes from the inlet to the outlet.

* * * * *